United States Patent
Chung et al.

(10) Patent No.: US 9,110,059 B2
(45) Date of Patent: Aug. 18, 2015

(54) BIO-PIN

(75) Inventors: Ji Hyung Chung, Seoul (KR); Yang Soo Jang, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/005,047

(22) PCT Filed: Mar. 15, 2012

(86) PCT No.: PCT/KR2012/001890
§ 371 (c)(1),
(2), (4) Date: Nov. 18, 2013

(87) PCT Pub. No.: WO2012/124998
PCT Pub. Date: Sep. 20, 2012

(65) Prior Publication Data
US 2014/0256034 A1    Sep. 11, 2014

(30) Foreign Application Priority Data

Mar. 15, 2011  (KR) .................. 10-2011-0022984
Jun. 8, 2011   (KR) .................. 10-2011-0055007
Jun. 8, 2011   (KR) .................. 10-2011-0055008

(51) Int. Cl.
| | | |
|---|---|---|
| A61K 38/00 | (2006.01) | |
| C12N 5/00 | (2006.01) | |
| C12N 5/02 | (2006.01) | |
| G01N 33/554 | (2006.01) | |
| A61K 47/48 | (2006.01) | |
| A61L 31/16 | (2006.01) | |
| A61K 49/00 | (2006.01) | |

(52) U.S. Cl.
CPC ........ *G01N 33/554* (2013.01); *A61K 47/48246* (2013.01); *A61K 49/0097* (2013.01); *A61L 31/16* (2013.01); *A61K 38/00* (2013.01); *A61L 2300/25* (2013.01); *C07K 2319/00* (2013.01); *C07K 2319/10* (2013.01); *C07K 2319/33* (2013.01); *C07K 2319/60* (2013.01)

(58) Field of Classification Search
None
See application file for complete search history.

(56) References Cited

FOREIGN PATENT DOCUMENTS

| CN | 102580091 A | | 7/2012 |
|---|---|---|---|
| WO | WO 99/16884 | * | 4/1999 |
| WO | WO-2007123667 A2 | | 11/2007 |
| WO | WO-2010002468 A1 | | 1/2010 |
| WO | WO-2010115052 A2 | | 10/2010 |

OTHER PUBLICATIONS

Janson et al, Protein D, the Immunoglobulin D-Binding Protein of *Haemophilus influenzae*, Is a Lipoprotein, Infection and Immunity, Apr. 1992, p. 1336-1342.*
Singhal et al, HIV-1 gp160 Protein-Macrophage Interactions Modulate Mesangial Cell Proliferation and Matrix Synthesis, American Journal of Pathology, vol. 147, No. 6, Dec. 1995.*
Aicher et al. "Assessment of the Tissue Distribution of Transplanted Human Endothelial Progenitor Cells by Radioactive Labeling." *Circulation*. 107.16(2003):2134-2139.

* cited by examiner

*Primary Examiner* — Karlheinz R Skowronek
*Assistant Examiner* — Sergio Coffa
(74) *Attorney, Agent, or Firm* — Mintz Levin Cohn Ferris Glovsky and Popeo, P.C.; Fred C. Hernandez; Shovon Ashraf

(57) ABSTRACT

A bio-pin is provided. The bio-pin can be used for cell transfer and treatment, cell tracing, and targeting of specific tissues and cells using a peptide-based complex in which a cell-penetrating peptide or a cell-adhesive peptide is bound to one or both ends of a cell membrane protein, and used in a molecular imaging system, a medical appliance, and the like.

17 Claims, 6 Drawing Sheets

FIG. 2

(a)
NcoI — His-Tag — Thrombin — NdeI
TATACCATGGGCAGCAGCCATCATCATCATCATCACAGCAGCGGCCTGGTGCCGCGCGGCAGCCATATG
MetGlySerSer HisHisHisHisHisHis SerSerGly LeuValProArgGlySer HisMet BamHI
TACGGCCGCAAGAAACGCCGCCAGCGCCGCCGC GGATCC CTG GCA ATC GCC ATC ACC GCG CTC TAC TCG GCC
Y G R K K R R Q R R R   G  S  L   A   I   A   I   T   A   L   Y   S   A
TAT GTG TGC GCC GTG GGG CTG CTG GGC AAC GTG CTT GTC ATG TTC GGC ATC GTC CGG TAC ACT
 V   C   A   V   G   L   L   G   N   V   L   V   M   F   G   I   V   R   Y   T XhoI
TACGGCCGCAAGAAACGCCGCCAGCGCCGCCGCTAA CTCGAG
Y G R K K R R Q R R R STOP
TAT (b)
NcoI — His-Tag — Thrombin — NdeI
TATACCATGGGCAGCAGCCATCATCATCATCATCACAGCAGCGGCCTGGTGCCGCGCGGCAGCCATATG
MetGlySerSer HisHisHisHisHisHis SerSerGly LeuValProArgGlySer HisMet BamHI
GGCCGCGGCGACAGCCCG GGATCC CTG GCA ATC GCC ATC ACC GCG CTC TAC TCG GCC
G R G D S P   G  S  L   A   I   A   I   T   A   L   Y   S   A
RGD GTG TGC GCC GTG GGG CTG CTG GGC AAC GTG CTT GTC ATG TTC GGC ATC GTC CGG TAC ACT
 V   C   A   V   G   L   L   G   N   V   L   V   M   F   G   I   V   R   Y   T XhoI
TACGGCCGCAAGAAACGCCGCCAGCGCCGCCGCTAA CTCGAG
Y G R K K R R Q R R R STOP (c)
NcoI — His-Tag — Thrombin — NdeI
TATACCATGGGCAGCAGCCATCATCATCATCATCACAGCAGCGGCCTGGTGCCGCGCGGCAGCCATATG
MetGlySerSer HisHisHisHisHisHis SerSerGly LeuValProArgGlySer HisMet BamHI
GGATCC CTG GCA ATC GCC ATC ACC GCG CTC TAC TCG GCC GTG TGC GCC GTG GGG
 G  S  L   A   I   A   I   T   A   L   Y   S   A   V   C   A   V   G CTG CTG GGC AAC GTG CTT GTC ATG TTC GGC ATC GTC CGG TAC ACT
 L   L   G   N   V   L   V   M   F   G   I   V   R   Y   T XhoI
TACGGCCGCAAGAAACGCCGCCAGCGCCGCCGCTAA CTCGAG
Y G R K K R R Q R R R STOP
TAT FIG. 10
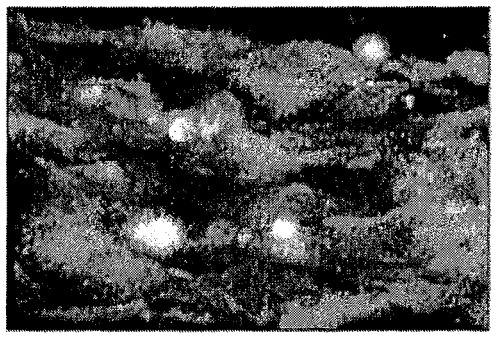
3D Image of CellMaskTM plasma membrane stains(red) of HUVECS and VybrantTM Dio (green) of monocyte THP-1 cells
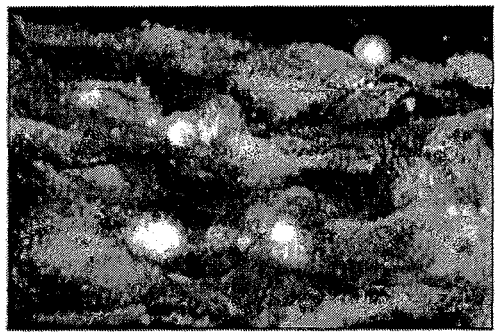
3D Image of CellMaskTM plasma membrane stains(red) of HUVECS and peptides stained with Dylight405 NHE-ester(blue) anchored in monocyte THP-1 cells

SEQUENCE LISTING

```
<160> NUMBER OF SEQ ID NOS: 23

<210> SEQ ID NO 1
<211> LENGTH: 31
<212> TYPE: PRT
<213> ORGANISM: Artificial Sequence
<220> FEATURE:
<223> OTHER INFORMATION: Human opioid receptor delta transmembrane 1

<400> SEQUENCE: 1

Leu Ala Ile Ala Ile Thr Ala Leu Tyr Ser Ala Val Cys Ala Val Gly
1               5                   10                  15

Leu Leu Gly Asn Val Leu Val Met Phe Gly Ile Val Arg Tyr Thr
            20                  25                  30

<210> SEQ ID NO 2
<211> LENGTH: 11
<212> TYPE: PRT
<213> ORGANISM: Artificial Sequence
<220> FEATURE:
<223> OTHER INFORMATION: Tat peptide derived from HIV

<400> SEQUENCE: 2

Tyr Gly Arg Lys Lys Arg Arg Gln Arg Arg Arg
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Integrin ligand

<400> SEQUENCE: 3

Arg Gly Asp Ser
1

<210> SEQ ID NO 4
<211> LENGTH: 6
<212> TYPE: PRT
<213> ORGANISM: Artificial sequence
<220> FEATURE:
<223> OTHER INFORMATION: Adhesive peptide for vascular smooth muscle
      cells

<400> SEQUENCE: 4

Lys Gln Ala Gly Asp Val
1               5
```

<210> SEQ ID NO 5
<211> LENGTH: 4
<212> TYPE: PRT
<213> ORGANISM: Artificial Sequence
<220> FEATURE:
<223> OTHER INFORMATION: Elastin-derived non-integrin ligand

<400> SEQUENCE: 5

Val Ala Pro Gly
1

<210> SEQ ID NO 6
<211> LENGTH: 12
<212> TYPE: PRT
<213> ORGANISM: Artificial Sequence
<220> FEATURE:
<223> OTHER INFORMATION: Adhesive peptide from fibronectin

<400> SEQUENCE: 6

Tyr Ala Val Thr Gly Arg Gly Asp Ser Pro Ala Ser
1               5                   10

<210> SEQ ID NO 7
<211> LENGTH: 20
<212> TYPE: PRT
<213> ORGANISM: Artificial Sequence
<220> FEATURE:
<223> OTHER INFORMATION: Adhesive peptide from collagen alpha1(IV) chain
<220> FEATURE:
<221> NAME/KEY: misc_feature
<222> LOCATION: (13)..(13)
<223> OTHER INFORMATION: Xaa can be any naturally occurring amino acid

<400> SEQUENCE: 7

Ala Thr Leu Gln Leu Gln Glu Gly Arg Leu His Phe Xaa Phe Asp Leu
1               5                   10                  15

Gly Lys Gly Arg
            20

<210> SEQ ID NO 8
<211> LENGTH: 13
<212> TYPE: PRT
<213> ORGANISM: Artificial Sequence
<220> FEATURE:
<223> OTHER INFORMATION: Adhesive peptide from collagen alpha1(IV) chain

<400> SEQUENCE: 8

Ala Gly Thr Phe Ala Leu Arg Gly Asp Asn Pro Gln Gly
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Adhesive peptide from collagen alpha1(IV) chain

<400> SEQUENCE: 9

Gly Glu Phe Tyr Phe Asp Leu Arg Leu Lys Gly Asp Lys Tyr
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Integrin ligand

```
<400> SEQUENCE: 10

Gly Arg Gly Asp Ser Pro
1               5

<210> SEQ ID NO 11
<211> LENGTH: 33
<212> TYPE: DNA
<213> ORGANISM: Artificial sequence
<220> FEATURE:
<223> OTHER INFORMATION: Primer-1 for preparing BPin-55

<400> SEQUENCE: 11
tcacgtggat ccctggcaat cgccatcacc gcg                              33

<210> SEQ ID NO 12
<211> LENGTH: 69
<212> TYPE: DNA
<213> ORGANISM: Artificial Sequence
<220> FEATURE:
<223> OTHER INFORMATION: Primer-2 for preparing BPin-55

<400> SEQUENCE: 12
aggcatctcg agttagcggc ggcgctggcg gcgtttcttg cggccgtaag tgtaccggac   60
gatgccgaa                                                           69

<210> SEQ ID NO 13
<211> LENGTH: 36
<212> TYPE: DNA
<213> ORGANISM: Artificial sequence
<220> FEATURE:
<223> OTHER INFORMATION: Primer for preparing BPin-44

<400> SEQUENCE: 13
tcgtcccata tgggatccct ggcaatcgcc atcacc                            36

<210> SEQ ID NO 14
<211> LENGTH: 54
<212> TYPE: DNA
<213> ORGANISM: Artificial sequence
<220> FEATURE:
<223> OTHER INFORMATION: Primer-1 for preparing BPin-RGD

<400> SEQUENCE: 14
tcgtcccata tgggccgcgg cgacagcccg ggatccctgg caatcgccat cacc        54

<210> SEQ ID NO 15
<211> LENGTH: 243
<212> TYPE: DNA
<213> ORGANISM: Artificial sequence
<220> FEATURE:
<223> OTHER INFORMATION: BPin-55 construct: TAT-OPRD-TAT
<220> FEATURE:
<221> NAME/KEY: CDS
<222> LOCATION: (7)..(234)

<400> SEQUENCE: 15 tatacc atg ggc agc agc cat cat cat cat cat cac agc agc ggc ctg     48
       Met Gly Ser Ser His His His His His His Ser Ser Gly Leu
         1               5                  10 gtg ccg cgc ggc agc cat atg tac ggc cgc aag aaa cgc cgc cag cgc    96
Val Pro Arg Gly Ser His Met Tyr Gly Arg Lys Lys Arg Arg Gln Arg
 15                  20                  25                  30 cgc cgc gga tcc ctg gca atc gcc atc acc gcg ctc tac tcg gcc gtg   144
Arg Arg Gly Ser Leu Ala Ile Ala Ile Thr Ala Leu Tyr Ser Ala Val
                 35                  40                  45
```

```
tgc gcc gtg ggg ctg ctg ggc aac gtg ctt gtc atg ttc ggc atc gtc        192
Cys Ala Val Gly Leu Leu Gly Asn Val Leu Val Met Phe Gly Ile Val
            50                  55                  60 cgg tac act tac ggc cgc aag aaa cgc cgc cag cgc cgc taactcgag          243
Arg Tyr Thr Tyr Gly Arg Lys Lys Arg Arg Gln Arg Arg
 65                  70                  75
```

<210> SEQ ID NO 16
<211> LENGTH: 76
<212> TYPE: PRT
<213> ORGANISM: Artificial sequence
<220> FEATURE:
<223> OTHER INFORMATION: Synthetic Construct

<400> SEQUENCE: 16

```
Met Gly Ser Ser His His His His His His Ser Ser Gly Leu Val Pro
1               5                   10                  15

Arg Gly Ser His Met Tyr Gly Arg Lys Lys Arg Arg Gln Arg Arg
                20                  25                  30

Gly Ser Leu Ala Ile Ala Ile Thr Ala Leu Tyr Ser Ala Val Cys Ala
            35                  40                  45

Val Gly Leu Leu Gly Asn Val Leu Val Met Phe Gly Ile Val Arg Tyr
        50                  55                  60

Thr Tyr Gly Arg Lys Lys Arg Arg Gln Arg Arg
65                  70                  75
```

<210> SEQ ID NO 17
<211> LENGTH: 228
<212> TYPE: DNA
<213> ORGANISM: Artificial Sequence
<220> FEATURE:
<223> OTHER INFORMATION: BPin-RGD construct: RGD-OPRD-TAT
<220> FEATURE:
<221> NAME/KEY: CDS
<222> LOCATION: (7)..(219)

<400> SEQUENCE: 17

```
tatacc atg ggc agc agc cat cat cat cat cat cac agc agc ggc ctg         48
       Met Gly Ser Ser His His His His His His Ser Ser Gly Leu
        1               5                   10 gtg ccg cgc ggc agc cat atg ggc cgc ggc gac agc ccg gga tcc ctg        96
Val Pro Arg Gly Ser His Met Gly Arg Gly Asp Ser Pro Gly Ser Leu
 15                  20                  25                  30 gca atc gcc atc acc gcg ctc tac tcg gcc gtg tgc gcc gtg ggg ctg       144
Ala Ile Ala Ile Thr Ala Leu Tyr Ser Ala Val Cys Ala Val Gly Leu
                35                  40                  45 ctg ggc aac gtg ctt gtc atg ttc ggc atc gtc cgg tac act tac ggc       192
Leu Gly Asn Val Leu Val Met Phe Gly Ile Val Arg Tyr Thr Tyr Gly
            50                  55                  60 cgc aag aaa cgc cgc cag cgc cgc cgc taactcgag                         228
Arg Lys Lys Arg Arg Gln Arg Arg Arg
 65                  70
```

<210> SEQ ID NO 18
<211> LENGTH: 71
<212> TYPE: PRT
<213> ORGANISM: Artificial Sequence
<220> FEATURE:
<223> OTHER INFORMATION: Synthetic Construct

```
<400> SEQUENCE: 18

Met Gly Ser Ser His His His His His Ser Ser Gly Leu Val Pro
1               5                   10                  15

Arg Gly Ser His Met Gly Arg Gly Asp Ser Pro Gly Ser Leu Ala Ile
            20                  25                  30

Ala Ile Thr Ala Leu Tyr Ser Ala Val Cys Ala Val Gly Leu Leu Gly
        35                  40                  45

Asn Val Leu Val Met Phe Gly Ile Val Arg Tyr Thr Tyr Gly Arg Lys
    50                  55                  60

Lys Arg Arg Gln Arg Arg
65                  70

<210> SEQ ID NO 19
<211> LENGTH: 210
<212> TYPE: DNA
<213> ORGANISM: Artificial Sequence
<220> FEATURE:
<223> OTHER INFORMATION: BPin-44 construct: OPRD-TAT
<220> FEATURE:
<221> NAME/KEY: CDS
<222> LOCATION: (7)..(201)

<400> SEQUENCE: 19 tatacc atg ggc agc agc cat cat cat cat cat cac agc agc ggc ctg      48
       Met Gly Ser Ser His His His His His Ser Ser Gly Leu
           1               5                   10 gtg ccg cgc ggc agc cat atg gga tcc ctg gca atc gcc atc acc gcg      96
Val Pro Arg Gly Ser His Met Gly Ser Leu Ala Ile Ala Ile Thr Ala
15              20                  25                  30 ctc tac tcg gcc gtg tgc gcc gtg ggg ctg ctg ggc aac gtg ctt gtc     144
Leu Tyr Ser Ala Val Cys Ala Val Gly Leu Leu Gly Asn Val Leu Val
            35                  40                  45 atg ttc ggc atc gtc cgg tac act tac ggc cgc aag aaa cgc cgc cag     192
Met Phe Gly Ile Val Arg Tyr Thr Tyr Gly Arg Lys Lys Arg Arg Gln
        50                  55                  60 cgc cgc cgc taactcgag                                                210
Arg Arg Arg
        65

<210> SEQ ID NO 20
<211> LENGTH: 65
<212> TYPE: PRT
<213> ORGANISM: Artificial Sequence
<220> FEATURE:
<223> OTHER INFORMATION: Synthetic Construct

<400> SEQUENCE: 20

Met Gly Ser Ser His His His His His Ser Ser Gly Leu Val Pro
1               5                   10                  15

Arg Gly Ser His Met Gly Ser Leu Ala Ile Ala Ile Thr Ala Leu Tyr
            20                  25                  30

Ser Ala Val Cys Ala Val Gly Leu Leu Gly Asn Val Leu Val Met Phe
        35                  40                  45

Gly Ile Val Arg Tyr Thr Tyr Gly Arg Lys Lys Arg Arg Gln Arg Arg
    50                  55                  60

Arg
65
```

```
<210> SEQ ID NO 21
<211> LENGTH: 44
<212> TYPE: PRT
<213> ORGANISM: Artificial Sequence
<220> FEATURE:
<223> OTHER INFORMATION: BPin-44: OPRD-TAT

<400> SEQUENCE: 21

Gly Ser Leu Ala Ile Ala Ile Thr Ala Leu Tyr Ser Ala Val Cys Ala
1               5                   10                  15

Val Gly Leu Leu Gly Asn Val Leu Val Met Phe Gly Ile Val Arg Tyr
            20                  25                  30

Thr Tyr Gly Arg Lys Lys Arg Arg Gln Arg Arg Arg
        35                  40

<210> SEQ ID NO 22
<211> LENGTH: 55
<212> TYPE: PRT
<213> ORGANISM: Artificial Sequence
<220> FEATURE:
<223> OTHER INFORMATION: BPin-55: TAT-OPRD-TAT

<400> SEQUENCE: 22

Tyr Gly Arg Lys Lys Arg Arg Gln Arg Arg Gly Ser Leu Ala Ile
1               5                   10                  15

Ala Ile Thr Ala Leu Tyr Ser Ala Val Cys Ala Val Gly Leu Leu Gly
            20                  25                  30

Asn Val Leu Val Met Phe Gly Ile Val Arg Tyr Thr Tyr Gly Arg Lys
        35                  40                  45

Lys Arg Arg Gln Arg Arg Arg
        50                  55

<210> SEQ ID NO 23
<211> LENGTH: 50
<212> TYPE: PRT
<213> ORGANISM: Artificial Sequence
<220> FEATURE:
<223> OTHER INFORMATION: BPin-RGD: RGD-OPRD-TAT

<400> SEQUENCE: 23

Gly Arg Gly Asp Ser Pro Gly Ser Leu Ala Ile Ala Ile Thr Ala Leu
1               5                   10                  15

Tyr Ser Ala Val Cys Ala Val Gly Leu Leu Gly Asn Val Leu Val Met
            20                  25                  30

Phe Gly Ile Val Arg Tyr Thr Tyr Gly Arg Lys Lys Arg Arg Gln Arg
        35                  40                  45

Arg Arg
    50
```

BIO-PIN

CROSS-REFERENCE TO RELATED APPLICATION

This application claims priority to and the benefit of Korean Patent Application No. 2011-0022984, 2011-0055007, and 2011-0055008, filed Mar. 15, Jun. 8, and Jun. 8, 2011, respectively, the disclosures of which are incorporated herein by reference in their entirety.

INCORPORATION-BY-REFERENCE OF SEQUENCE LISTING

The contents of the text file named "46278_503N01US_ST25.txt", which was created on May 2, 2014 and is 11.1 KB in size, are hereby incorporated by reference in their entirety.

BACKGROUND

1. Field of the Invention

The present invention relates to a bio-pin which is a peptide-based complex capable of being used for cell transfer, tracing, and treatment, and used in a molecular imaging system and a medical appliance such as a stent.

2. Discussion of Related Art

In recent years, there has been a need for development of bio-materials capable of regulating adhesive strength in the field of applications using stem cells, such as cell transplantation, tissue transplantation, nanotubes, nanowires, microelectromechanical systems (MEMS), nanoparticles, biosensors, biochips, drug delivery, etc. (Nahar et al., 2006, *Crit. Rev Ther Drug Carrier Syst*, 23, 259-318). However, when endothelial progenitor cells (EPCs) which can be used as transfer cells for treatment of myocardial infarction are transferred to cardiac muscular tissues, most of the transferred cells are washed off at the beginning of cell transfer, and only 3 to 5% of the transferred cells are attached to the target tissues, indicating poor efficiency of the stem cell transfer (Aicher et al., 2003, *Circulation*, 107, 2134-2139). Since most of the other transfer cells exhibit similar results, there has been various attempts conducted to overcome these problems, but no outstanding methods are found. In particular, there has been research conducted to improve a cell attachment effect by transferring a gene encoding an adhesion protein to cells (Sheyn et al., 2010, *Adv Drug Deliv Rev.*, 62, 683-698). However, since the cells in which the gene is overexpressed may be highly regulated as genetically modified cells in clinical applications in the near future, it is difficult to commercialize technology using these cells.

There is research conducted so far to develop bioadhesives using a bio-friendly material in various fields. Typically, an adhesive extracted from a soybean, a urethane-based foam adhesive commercially available from Naturalock, a starch-based adhesive, a blue mussel (*Mytilus Edulis*)-derived adhesive, and a sea mussel-derived protein adhesive have been developed for industrial and medical uses (Ciannamea et al., 2010, *Bioresour Technol*, 101, 818-825; Luhrs and Geurtsen, 2009, *Prog Mol Subcell Biol*, 47, 359-380; Valenta, 2005, *Adv Drug Deliv Rev*, 57, 1692-1712; Silverman and Roberto, 2007, *Mar Biotechnol*, 9, 661-681). However, the bioadhesives are more environmentally friendly than other polymer-based adhesives such as epoxy or phenol resins, but their main aim is based on development of a much powerful type of material for use for surgical sutures or as industrial adhesives. Therefore, it is not suitable to directly apply an adhesive to cells to be transferred for cell treatment and transplantation.

Also, a molecular imaging system, which determines whether the cells to be transferred for cell treatment and transplantation are transferred in vivo or diagnoses diseases, has been used to yield an SPECT-CT image by separating monocytes at a level of an animal model and introducing $^{111}$indium oxine into the monocytes (Kircher et al., 2008, *Circulation*, 117, 388-395), or a study of imaging macrophages using an iodine or gold-nanoparticle contrast agent has been conducted (Hyafil et al., 2007, *Nat Med*, 13, 636-641). However, such nanoparticles have the serious limitation of diagnosis in that they exude from cells and spread throughout the body.

SUMMARY OF THE INVENTION

The present invention is directed to providing a bio-pin which is a peptide-based complex for binding in vivo, which induces an increase in intercellular adhesion, and a method of preparing the same.

Also, the present invention is directed to providing uses of the bio-pin which is the peptide-based complex, such as cell transfer, cell treatment, diagnosis, medical tools, and the like.

One aspect of the present invention provides a peptide-based complex represented by the following Structural Formula 1:

[Structural Formula 1]

[Structural Formula 2]

wherein, A and B each independently represent a cell-penetrating peptide, cell-adhesive peptide, or a cell-penetrating or cell-adhesive peptide bound to a monocyte or an oncotropic cell, and A' represents a cell-penetrating or cell-adhesive peptide bound to a monocyte or an oncotropic cell.

Another aspect of the present invention provides a contrast agent composition including the peptide-based complex according to the present invention.

Still another aspect of the present invention provides a targeted contrast agent composition including the peptide-based complex according to the present invention.

Still another aspect of the present invention provides a composition for simultaneous diagnosis or treatment, which includes the peptide-based complex according to the present invention.

Still another aspect of the present invention provides a multi-diagnostic probe including the peptide-based complex according to the present invention, and a diagnostic probe.

Still another aspect of the present invention provides a cellular therapeutic agent including the peptide-based complex according to the present invention.

Yet another aspect of the present invention provides a medical stent including the peptide-based complex according to the present invention.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which:

FIG. 1a shows a configuration in which the cell-penetrating peptides are fused with both ends of the cell membrane protein, FIG. 1b shows a configuration in which the cell-penetrating peptide and the cell-adhesive peptide are fused with both ends of the cell membrane protein, FIG. 1c shows a configuration in which the cell-penetrating peptide and a fluorescent material are fused with both ends of the cell membrane protein and a cell exhibiting targetability is bound to the cell membrane protein, FIG. 1d shows a configuration in which the cell-penetrating peptide is fused with one end of the cell membrane protein, which leads to formation of a fusion peptide which does not form an intercellular bond since the cell-penetrating peptide is not bound to the other end of the cell membrane protein, and FIG. 1e shows an action mechanism in which the peptide-based complex shown in the configuration of FIG. 1c specifically binds to a lesion site through transfer of the peptide-based complex to a cell or a tissue;

FIG. 2 is a diagram showing amino acid sequences of the peptide-based complexes according to the present invention in which a cell-penetrating peptide or a cell-adhesive peptide is fused with the N-terminus or C-terminus of a cell membrane protein; FIG. 2a shows a configuration in which the cell-penetrating peptides (TAT) are bound to the N-terminus and C-terminus of the cell membrane protein using the cell membrane protein as a fragment of opioid receptor-δ transmembrane domain 1 (OPRD), FIG. 2b shows a configuration in which the cell-penetrating peptide (TAT) and the cell-adhesive peptide (RGD) are bound to the N-terminus and C-terminus of the cell membrane protein, and FIG. 2c shows a configuration in which the cell-penetrating peptide (TAT) is bound to the C-terminus of the cell membrane protein;

FIG. 10 is a diagram showing three-dimensional (3D) images obtained in the procedure shown in FIG. 8: one image (left panel) taken together after HUVECs (red) spread on a petri dish is overlapped by THP-1 (green), and the other image (right panel) showing that the peptide-based complex BPin-44 (blue) modified with Dylight 405 NHE-ester is anchored in THP-1.

DETAILED DESCRIPTION OF EXEMPLARY EMBODIMENTS

Figure 1:
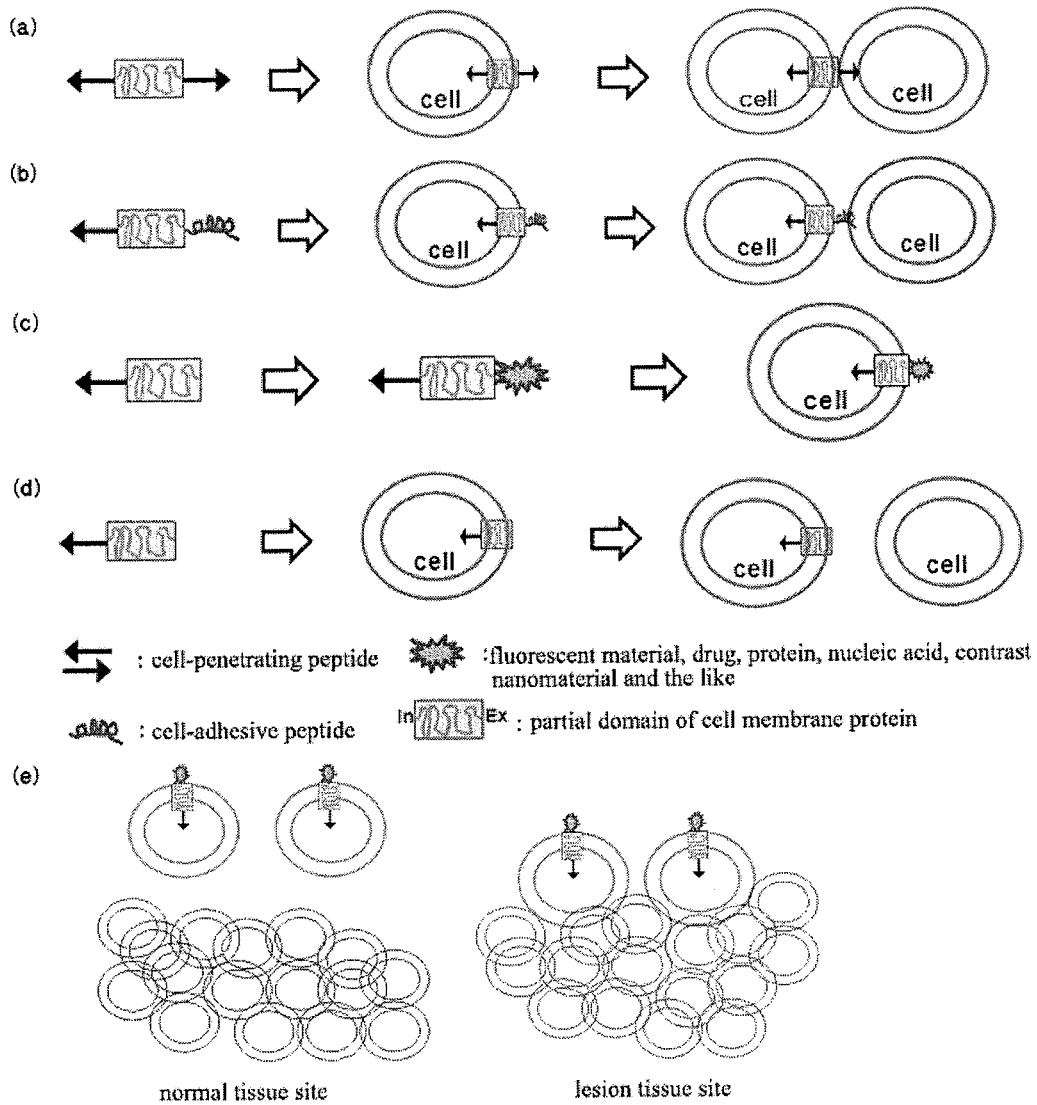
FIG. 1 is a schematic diagram showing a peptide-based complex according to the present invention in which a cell-penetrating peptide and a cell-adhesive peptide are fused with the N-terminus and/or the C-terminus of a cell membrane protein, respectively, and intercellular bonds of the peptide-based complex.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The present invention has aimed at developing a bio-pin capable of simply increasing a physical bond between cells without transferring a specific gene, a biological change of which is difficult to predict in cells and which may give rise to side effects, into the cells and overexpressing the specific gene.

In the cell transfer and cell treatment technologies, a treatment effect may be generally varied depending on how effectively the transfer cells adhere to a target organ or tissue. Methods of overexpressing a specific gene or various attempts to efficiently transfer the transfer cells to a target tissue using a polymer compound disprove the evidence against the variation of the treatment effect.

Therefore, unlike the conventional genetic engineering methods or cell transfer technology using a polymer, development of a bio-pin to be transferred by anchoring a peptide-based pin in transfer cells presents the probability as a material in the field of cell transfer and cell treatment, and nanotechnology using the cell transfer and cell treatment.

Therefore, the present invention provides a peptide-based complex represented by the following Structural Formula 1:

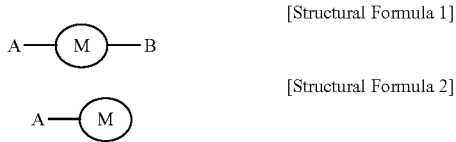

[Structural Formula 1]

[Structural Formula 2]

wherein, A and B each independently represent a cell-penetrating peptide, a cell-adhesive peptide, or a cell-penetrating or cell-adhesive peptide bound to a monocyte or an oncotropic cell, and A' represents a cell-penetrating or cell-adhesive peptide bound to a monocyte or an oncotropic cell.

The peptide-based complex of the present invention represented by Structural Formula 1 may have a cell-penetrating peptide/cell membrane protein/cell-penetrating peptide structure, a cell-penetrating peptide/cell membrane protein/cell-adhesive peptide structure, a cell-adhesive peptide/cell membrane protein/cell-penetrating peptide structure, or a cell-adhesive peptide/cell membrane protein/cell-adhesive peptide structure. The structure may be a structure in which cells for use as an cellular therapeutic agent, such as, for example, stem cells, immune cells, endothelial cells, vascular progenitor cells, and the like, a pharmaceutically active component for diagnosis and treatment of diseases, a tissue-specific binding component, a fluorescent material, a nanomaterial, and/or a contrast agent are bound to the cell-penetrating peptide (or cell-adhesive peptide).

The peptide-based complex of the present invention represented by Structural Formula 1 or 2 may have a targetable cell/cell-penetrating peptide (or cell-adhesive peptide)/cell membrane protein structure, or a targetable cell/cell-penetrating peptide (or cell-adhesive peptide)/cell membrane protein/cell-penetrating peptide (or cell-adhesive peptide) structure. The structure may be a structure in which a pharmaceutically active component for diagnosis and treatment of diseases, a fluorescent material, a nanomaterial, and/or a contrast agent are bound to the cell-penetrating peptide (or cell-adhesive peptide). The targetable cells may include lesion-friendly cells such as monocytes or oncotropic cells. The lesion-friendly cells may be cells which can recognize cells of a lesion site to specifically bind to the cells. For example, the lesion-friendly cells may recognize cells of an arteriosclerotic lesion site, a tumor site, and the like.

Binding between the cell-penetrating peptide or cell-adhesive peptide and the cell membrane protein may be accomplished through a peptide bond, or be accomplished directly through a chemical, physical covalent or non-covalent bond or using other mediator, but the present invention is not particularly limited thereto.

The fluorescent material, the pharmaceutically active component, the tissue-specific binding component, the nanoparticles, and the like may be bound to the peptide-based complex of the present invention directly by means of a chemical, physical covalent or a non-covalent bond or using other mediator, but the present invention is not particularly limited thereto.

In the cell membrane protein, a binding site of the cell-penetrating peptide or the cell-adhesive peptide may be selected without limitation, and may, for example, bind to one or both ends of the cell membrane protein.

When the targetable cell binds to the peptide-based complex according to the present invention, the cell-penetrating peptide or the cell-adhesive peptide of the peptide-based complex may be connected by penetrating or binding a cell membrane of the targetable cell.

In the cell membrane protein, the binding site of the cell-penetrating peptide or the cell-adhesive peptide may be selected without limitation, and may, for example, bind to one or both ends of the cell membrane protein.

In this specification, the term "bio-pin" refers to a biological material, for example, a peptide-based complex for fixing cells. In particular, two elements used in the bio-pin are composed of a specific membrane protein and a cell-penetrating peptide (or a cell-adhesive peptide) present in a mammal cell, and may have a pin structure in which the specific membrane protein of the cell forms a head portion and the cell-penetrating peptide (or cell-adhesive peptide) bound to one or both ends of the membrane protein forms a tail portion.

According to one exemplary embodiment, in case of the peptide-based complex designed to position a specific membrane protein of a cell in the middle thereof and fuse the cell-penetrating peptide (or cell-adhesive peptide) with both an intracellular site and an extracellular site of the membrane protein, when the peptide-based complex is transferred to cells, the cell-penetrating peptide positioned in a cell membrane to be fused with the intracellular site is directed inward from the cells, and the cell-penetrating peptide (or cell-adhesive peptide) fused with the extracellular site is externally exposed to the cells, which makes it possible to anchor or adhere the peptide-based complex in/to a target cell or tissue (see FIG. 1). Anchoring or adhering the externally exposed peptide-based complex in/to the target cell or tissue to enhance an intercellular bond proves that, when the peptide-based complex having a structure in which the cell-penetrating peptide is fused with only an intracellular domain of the membrane protein is transferred to cells, the peptide-based complex is positioned in the cell membrane but is not anchored in the target cell or tissue since there is no cell-penetrating peptide (or cell-adhesive peptide) externally exposed to the cells (see FIG. 1).

According to another exemplary embodiment, a specific membrane protein of a cell is positioned in the middle, and an intracellular site and an extracellular site of the membrane protein are positioned so that a cell-penetrating peptide is fused with the intracellular site, and a fluorescent material, a contrast agent, a nanomaterial, and the like are fused with the extracellular site, thereby preparing a peptide-based complex. When the peptide-based complex is transferred to a target cell, the peptide-based complex is positioned in a cell membrane so that the cell-penetrating peptide fused with the intracellular site can be directed inward from the cells, and the fluorescent material, the contrast agent, the nanomaterial, and the like can be externally exposed to the cells, which makes it possible to recognize a target cell or tissue (see FIG. 1). In general, the target cell may select cells having strong binding affinity to a lesion site of a specific disease. For example, the target cell may include monocytes, tumor-friendly natural killer cells, or macrophages. When the target cell in which the peptide-based complex is bound to a cell membrane is transferred to cells or tissues, the target cell recognizes the lesion site to cause an increase in binding affinity to cells of the lesion site (see FIG. 1). Therefore, a tissue-specific binding component exhibiting targetability is not further required.

The term "peptide-based complex" noted in this specification refers to a fusion peptide in which at least two peptides are bound to each other. Here, a complex in which a cell is bound to one of the two peptides is also referred to as the peptide-based complex. It will be understood that a method of preparing a peptide-based complex as will be described below is associated with preparation of a fusion peptide to which no cells are bound.

The term "oncotropic cells" noted in this specification refers to cells having strong affinity to tumor cells. For example, the oncotropic cells may include natural killer cells, macrophages, and the like.

The term "targetable cells" noted in this specification refers to cells having affinity to tissues or cells of a lesion site. In particularly, examples of the targetable cells may include cells from an arteriosclerotic lesion site, a tumor site, and the like. Therefore, the targetable cells may include monocytes or oncotropic cells, the monocytes may include THP-1, and the kinds of the oncotropic cells are as described above.

The cell membrane protein is not particularly limited as long as it is a membrane protein from mammal cells. Preferably, the cell membrane protein may be a transmembrane domain. For example, cell membrane proteins are not particularly limited as long as they does not affect the death of cells including opioid receptor-δ transmembrane domain 1 (OPRD TM1), and the like. For example, an amino acid sequence set forth in SEQ ID NO: 1 may be used as the cell membrane protein.

The cell-penetrating peptide (CPP) or the protein transduction domain (PTD) refers to a peptide which can transfer a specific protein, a virus, DNA, RNA, a fat, a carbohydrate, or a chemical compound, which is bound directly through a chemical, physical covalent or non-covalent bond with the cell-penetrating peptide (CPP) or the protein transduction domain (PTD) or indirectly using other mediator, into the cytoplasm or nucleus of a eukaryotic or prokaryotic cell.

The cell-penetrating peptide is not particularly limited. However, a trans-activating transcriptional activator (Tat) protein derived from human immunodeficiency virus type I (HIV-1), an Antp (Antennapedia or penetratin) peptide which is a *Drosophila* Antennapedia homeodomain, a rat transcription factor Mph-1, VP22 of HSV-1, and HP4 of a herring protamine may be used as the cell-penetrating peptide.

Also, the cell-penetrating peptide may include a cell-specific PTD exhibiting specificity in a specific cell type or state. One example of such a cell-specific PTD is an Hn1 synthetic peptide disclosed in U.S. Publication Patent No. 2002-0102265.

Further, the cell-penetrating peptide may be a synthetic peptide. One example of such a synthetic peptide is a peptide in which a HIV Tat protein of which $47^{th}$ to $57^{th}$ residues are modified by Ho et al. to optimize protein transduction potential (Ho et al. (2001) *Cancer Res* 61 (2):474-7).

In one specific exemplary embodiment of the present invention, the cell-penetrating peptide contains an HIV Tat: YGRKKRRQRRR (SEQ ID NO: 2).

The cell-adhesive peptide refers to a bioactive ligand covalently bound to a scaffold to improve cell adhesion or biologically specific cell adhesion when the scaffold is used as a mechanical support for cell growth and tissue formation in the field of tissue engineering and wound treatment. In this case, an amino acid sequence set forth in at least one selected from the group consisting of SEQ ID NO: 3 (RODS), SEQ ID NO: 4 (KQAGDV), SEQ ID NO: 5 (VAPG), SEQ ID NO: 6 (YAVTGRGDSPAS, FIB1), SEQ ID NO: 7 (ATLQLQEGR-LHFXFDLGKGR, EF1zz), SEQ ID NO: 8 (AGTFALRGD-NPQG, A99), and SEQ ID NO: 9 (GEFYFDLRLKGDKY, 531), or an amino acid sequence including at least one of the amino acid sequences, for example, an amino acid sequence set forth in SEQ ID NO: 10 (GRGDSP), may be used herein, but the present invention is not particularly limited thereto.

According to one exemplary embodiment of the present invention, the peptide-based complex of the present invention may have a structure in which the amino acid sequence set forth in SEQ ID NO: 2 is bound to one or both ends of the amino acid sequence set forth in SEQ ID NO: 1.

According to another exemplary embodiment of the present invention, the peptide-based complex of the present invention may have a structure in which the cell-penetrating peptide (SEQ ID NO: 2) and the cell-adhesive peptide (SEQ ID NO: 3) are bound to both ends of a cell membrane protein containing the amino acid sequence set forth in SEQ ID NO: 1.

According to another exemplary embodiment of the present invention, the peptide-based complex of the present invention may have a structure in which the amino acid sequence set forth in SEQ ID NO: 2 is bound to one or both ends of the amino acid sequence set forth in SEQ ID NO: 1. Here, a targetable cell may bind to the peptide-based complex.

The peptide-based complex according to the present invention may be prepared by means of methods known in the related art to synthesize peptides. For example, the peptide-based complex may be prepared by an in vitro synthesis method using a genetic recombination or protein expression system or a peptide synthesizer.

Therefore, the present invention provides a recombinant vector expressing the peptide-based complex.

In the present invention, the term "recombinant vector" refers to a vector which can express a desired protein in a proper host cell, that is, a gene construct including an essential regulatory element operatively connected to express a gene insert.

The vector includes a plasmid vector, a cosmid vector, a bacteriophage vector, and a viral vector, but the present invention is not limited thereto. The proper expression vector includes a signal sequence or a leader sequence for membrane targeting or secretion in addition to the expression-regulatory elements such as a promoter, an operator, an initiation codon, a stop codon, a polyadenylation signal, and an enhancer, and may be prepared by various methods according to a purpose. The promoter of the vector may be constitutive or inducible. Also, the expression vector includes a selection marker for selecting a host cell containing the vector. By way of example, a reproducible expression vector includes a replication origin.

The recombinant vector according to the present invention may be preferably prepared by inserting a nucleic acid sequence encoding a cell membrane protein into a conventional *Escherichia coli* (*E. coli*) strain expression vector, pHis/TAT. According to one exemplary embodiment of the present invention, the pHis/TAT vector was used as the *E. coli* strain expression vector, but the present invention is not limited thereto. For example, all the *E. coli* strain expression vectors which can be generally used herein may be used without limitation.

According to one exemplary embodiment of the present invention, the pHis/TAT vector which is the *E. coli* strain expression vector is used to insert a DNA fragment containing a gene encoding the OPRD TM1 domain of the present invention and a gene encoding the cell-penetrating peptide, thereby to prepare a recombinant vector (see FIG. 2).

According to another exemplary embodiment of the present invention, the pHis/TAT vector which is the *E. coli* strain expression vector is used to insert a DNA fragment containing a gene encoding the OPRD TM1 domain of the present invention, a gene encoding the cell-penetrating peptide and a gene encoding the cell-adhesive peptide, thereby to prepare a recombinant vector (see FIG. 2).

In addition, the present invention provides a transformant transformed with the recombinant vector expressing the peptide-based complex according to the present invention.

The transformation includes any methods of introducing a nucleic acid sequence into an organism, cells, tissues, or organs, and a suitable standard technique may be selected according to a host cell, and performed as known in the related art. Such a method may include electroporation, protoplast fusion, calcium phosphate (CaPO$_4$) precipitation, calcium chloride (CaCl$_2$) precipitation, agitation using a silicon carbide fiber, *Agrobacteria*-mediated transformation, PEG, dextran sulfate, lipofectamine, and the like, but the present invention is not limited thereto.

Also, since an expression level and modification of a protein are varied according to the host cell, the host cell most suitable for the purpose may be selected and used.

The host cell may include prokaryotic host cells such as *E. coli, Bacillus subtilis, Streptomyces* sp., *Pseudomonas* sp., *Proteus mirabilis*, or *Staphylococcus* sp., but the present invention is not limited thereto. Also, lower eukaryotic cells such as fungi (for example, *Aspergillus* sp.), and yeasts (for example, *Pichia pastoris, Saccharomyces cerevisiae, Schizosaccharomyces* sp., and *Neurospora crassa* sp.), and higher eukaryote-derived cells such as insect cells, plant cells, and mammal cells may be used as the host cell.

The transformant may be easily prepared by introducing the recombinant vector into any host cell. According to one exemplary embodiment of the present invention, the transformant may be prepared by introducing the recombinant vector pHis/TAT into an *E. coli* strain BL21 (DE3).

Also, the present invention provides a method of preparing a peptide-based complex, which includes separating and purifying a culture broth of the transformant transformed with the recombinant vector expressing the peptide-based complex according to the present invention.

Preferably, the peptide-based complex may be obtained by culturing and purifying the transformant according to a conventional culture method. An amino acid sequence of the peptide-based complex may be partially modified to any extent to which the modified amino acid sequence does not affect the ability to produce cytokines according to an insert introduced into the recombinant vector, that is, a base sequence of a coding gene. The modification means a change by deletion, insertion, or substitution.

In addition, the present invention provides a polyclonal antibody specifically binding to the peptide-based complex according to the present invention.

A method of preparing the polyclonal antibody is not particularly limited, but the polyclonal antibody may be prepared according to the following method.

A specific pathogen-free (SPF) animal is injected once to several times with the peptide-based complex of the present invention to be immunized. Within a predetermined time after the final immunization, whole blood is collected, and serum is extracted from the whole blood to obtain a polyclonal antibody against the protein of the present invention.

The immunized animal is not particularly limited as long as it is an animal used for typical immunization. For example, the immunized animal may be a rat. The number and duration of injections for immunization, and an administration method are not particularly limited since they may be changed or modified at a level of a person having ordinary skill in the art.

Also, the peptide-based complex according to the present invention may be modified with a fluorescent material.

The fluorescent material may be linked directly by means of a chemical, physical covalent or non-covalent bond with the cell-penetrating peptide or the cell-adhesive peptide, or linked indirectly using other mediator.

The fluorescent material may include a Dylight 488 NHE-ester dye, Vybrant™ DiI, Vybrant™ DiO, quantum dot nanoparticles, fluorescein, rhodamine, lucifer yellow, B-phycoerythrin, 9-acridine isothiocyanate, lucifer yellow VS, 4-acetamido-4'-isothio-cyanatostilbene-2,2'-disulfonic acid, 7-diethylamino-3-(4'-isothiocyanatophenyl)-4-methylcoumarin, succinimidyl-pyrenebutyrate, a 4-acetamido-4'-isothiocyanatostilbene-2,2'-disulfonic acid derivative, LC™-Red 640, LC™-Red 705, Cy5, Cy5.5, lissamine, isothiocyanate, erythromycin isothiocyanate, diethylenetriamine pentaacetate, 1-dimethylaminonaphthyl-5-sulfonate, 1-anilino-8-naphthalene sulfonate, 2-p-toluidinyl-6-naphthalene sulfonate, 3-phenyl-7-isocyanatocoumarin, 9-isothiocyanatoacridine, acridine orange N-(-p-(2-benzoxazoylyl)phenyl)maleimide thiadiazole, stilbene, pyrene, an Even conductor, silica including a fluorescent material, Group II/IV semiconductor quantum dots, Group III/V semiconductor quantum dots, Group IV semiconductor quantum dots, or a mixed structure of multiple components, but the present invention is not particularly limited thereto Preferably, at least one selected from the group consisting of quantum dot nanoparticles, Cy3.5, Cy5, Cy5.5, Cy7, indocyanine green (ICG), Cypate, ITCC, NIR820, NIR2, IRDye78, IRDye80, IRDye82, Cresy Violet, Nile Blue, Oxazine 750, Rhodamine-800, lanthanides, and Texas Red may be used as the fluorescent material, and Group II-VI or III-V compounds may be used as the quantum dot nanoparticles. In this case, at least one selected from the group consisting of CdSe, CdSe/ZnS, CdTe/CdS, CdTe/CdTe, ZnSe/ZnS, ZnTe/ZnSe, PbSe, PbS, InAs, InP, InGaP, InGaP/ZnS and HgTe may be used as the quantum dot nanoparticles.

Also, the peptide-based complex according to the present invention may be used for treatment of diseases by introducing a pharmaceutically active component directly by means of a chemical, physical covalent or non-covalent bond or indirectly using other mediator.

The pharmaceutically active component may include siRNA, antisense, an anti-cancer agent, an antibiotic agent, a hormone, a hormone antagonist, an interleukin, an interferon, a growth factor, a tumor necrosis factor, an endotoxin, a lymphotoxin, urokinase, streptokinase, a tissue plasminogen activator, a protease inhibitor, alkylphosphocholine, a component labeled with a radioactive isotope, a cardiovascular drug, a gastrointestinal drug, and a nervous system drug, which may be used alone or in combination, but the present invention is not particularly limited thereto.

The anti-cancer agent is not particularly limited, but, may, for example, include Epirubicin, Docetaxel, Gemcitabine, Paclitaxel, cisplatin, carboplatin, taxol, procarbazine, cyclophosphamide, dactinomycin, daunorubicin, etoposide, tamoxifen, doxorubicin, mitomycin, bleomycin, plicomycin, transplatinum, vinblastin, or methotrexate.

Also, the peptide-based complex according to the present invention may be provided with targetability by introducing a tissue-specific binding component directly by means of a chemical, physical covalent or non-covalent bond or indirectly using other mediator.

The tissue-specific binding component may include an antigen, an antibody, RNA, DNA, a hapten, avidin, streptavidin, neutravidin, Protein A, Protein G, lectin, selectin, a radioactive isotope-labeled component, or a tumor marker, which may be used alone or in combination, but the present invention is not particularly limited thereto.

In addition, the cell-penetrating peptide may include a cell-specific PTD exhibiting specificity in a specific cell type or state, for example, an Hn1 synthetic peptide disclosed in U.S. Publication Patent No. 2002-0102265, so that the peptide-based complex according to the present invention can have targetability.

Also, the present invention is directed to providing a contrast agent composition including the peptide-based complex of the present invention.

The peptide-based complex according to the present invention may be used as a contrast agent capable of imaging a target part using a magnetic-resonance and optical imaging system since a fluorescent material is chemicophysically bound to the peptide-based complex.

The contrast agent composition according to the present invention may further include a pharmaceutically available carrier. The carrier includes a carrier and a vehicle, which are widely used in the field of medicine. More particularly, the carrier includes an ion exchange resin, alumina, aluminum stearate, lecithin, a serum protein (for example, human serum albumin), a buffering substance (for example, various phosphates, glycine, sorbic acid, calcium sorbate, a partial glyceride mixture with saturated vegetable fatty acid), water, a salt or electrolyte (for example, protamine sulfate, sodium dihydrogen phosphate, potassium hydrogen phosphate, sodium chloride, and a zinc salt), colloidal silica, magnesium trisilicate, polyvinylpyrrolidone, cellulose-based substrate, polyethylene glycol, sodium carboxymethylcellulose, polyarylate, wax, polyethylene glycol, or wool fat, but the present invention is not limited thereto.

Also, the contrast agent composition according to the present invention may further include a lubricant, a wetting agent, an emulsifying agent, a suspending agent, or a preservative in addition to the above-described components.

In one aspect, the contrast agent composition according to the present invention may be prepared in a soluble solution for parenteral administration. Preferably, a buffering solution such as a Hank's solution, a Ringer's solution, or physically buffered saline may be used. A substrate which can increase viscosity of a soluble injection suspension, such as sodium carboxymethylcellulose, sorbitol, or dextran, may be added to the suspension.

Another preferred aspect of the contrast agent composition according to the present invention may be in the form of a sterile injectable preparation such as a sterile injectable aqueous or oily suspension. Such a suspension may be formulated according to a technique known in the related art using a proper dispersing or wetting agent (for example, Tween 80), and a suspending agent.

Also, the sterile injectable preparation may be a sterile injectable solution or suspension in a nontoxic, parenterally available diluent or solvent (for example, a solution in 1,3-butanediol). The vehicle and solvent which may be used herein includes mannitol, water, a Ringer's solution, and an isotonic sodium chloride solution. In addition, sterile nonvolatile oil may be typically used as a solvent or a suspending medium. For this purpose, any of less pungent nonvolatile oils may be used since they include synthetic mono- or di-glyceride.

When the contrast agent composition according to the present invention is administered into tissues or cells separated from a target to be diagnosed, the contrast agent composition may be used to detect a signal emitted by a fluorescent peptide-based complex to obtain an image.

In this case, a magnetic resonance imaging system (MRI) and an optical imaging system may be preferably used to detect the signal emitted from the fluorescent peptide-based complex.

The magnetic resonance imaging system is a device for imaging a biological tissue by putting the biological tissue in the strong magnetic field, irradiating the biological tissue with specific frequency waves so that the atomic nuclei such as hydrogen present in the biological tissue can absorb energy to be in a high energy state, suspending the wave irradiation to emit the energy of the atomic nuclei such as hydrogen, converting the energy into signals, and imaging the signals processed with a computer. Since magnetism or waves are hindered by bones, clear 3D tomographic images may be obtained for tumors in the surroundings of the hard skulls, or brains or bone marrows at any angles in a vertical or horizontal direction. In particular, the magnetic resonance imaging system may be a T2 spin-spin relaxation magnetic resonance imaging system.

Also, the present invention is directed to providing a targeted contrast agent composition including the peptide-based complex according to the present invention.

The peptide-based complex according to the present invention may exhibit fluorescence since a fluorescent material is bound to the peptide-based complex. Also, the peptide-based complex may be targetable since a tissue-specific binding component may further bind to the peptide-based complex. As a result, the peptide-based complex according to the present invention may be used as a contrast agent capable of imaging a target site using a magnetic-resonance and optical imaging system.

Also, in case of the peptide-based complex in which a targetable cell is bound to the cell-penetrating peptide according to the present invention, it is possible to diagnose diseases without using a separate tissue-specific binding component by delivering cells such as monocytes, natural killer cells, or macrophages, which have specific affinity to a specific lesion site, into the lesion tissue site upon in vivo introduction of the peptide-based complex since the cells are bound to the targetable cell. For example, the lesion tissue site may be an arteriosclerotic lesion tissue or a tumor tissue.

Also, the present invention is directed to providing a composition for simultaneous diagnosis or treatment, which includes the peptide-based complex according to the present invention.

The peptide-based complex according to the present invention may exhibit fluorescence since a fluorescent material is bound to the peptide-based complex. At the same time, since the peptide-based complex according to the present invention chemicophysically binds to the pharmaceutically active component, the peptide-based complex may be used as a nanoprobe and a drug for separation, diagnosis, or treatment of biological molecules by means of a magnetic-resonance and optical imaging system, or used as a gene delivery vehicle.

One representative example of the in vivo diagnosis using the peptide-based complex may include a molecular magnetic resonance imaging or magnetic relaxation sensor. As the peptide-based complex increases in size, the peptide-based complex shows a higher T2 contrast effect. Using this property, the peptide-based complex may be used as a sensor for detecting biological molecules. That is, when entanglement of the peptide-based complex is induced by certain biological molecules, a T2 magnetic resonance imaging effect is improved. This difference may be used to detect the biological molecules.

Also, the peptide-based complex according to the present invention may be used to diagnose and/or treat arteriosclerosis, or various diseases associated with a tumor, for example, gastric cancer, lung cancer, breast cancer, ovarian cancer, liver cancer, bronchogenic cancer, nasopharyngeal cancer, laryngeal cancer, pancreatic cancer, bladder cancer, colon cancer, and cervical cancer.

According to one exemplary embodiment, when the peptide-based complex of the present invention is bound to monocytes, the monocytes may recognize cells of an arteriosclerotic lesion site, and bind to the cells. As a result, it is possible to diagnose arteriosclerosis through fluorescence of the fluorescent material bound to a portion of the peptide-based complex, or specifically treat the arteriosclerosis using a drug capable of treating arteriosclerosis bound to the peptide-based complex.

According to another exemplary embodiment, when the peptide-based complex of the present invention is bound to the oncotropic cells such as natural killer cells, macrophages, and the like, the oncotropic cells may recognize cancer cells, and bind to the cancer cells. As a result, it is possible to diagnose a cancer through the fluorescence of the fluorescent material bound to a portion of the peptide-based complex, or specifically treat the cancer using a drug capable of treating cancer bound to the peptide-based complex.

According to still another exemplary embodiment, the tumor cells expressing and/or secreting a specific substance which is hardly or never produced in normal cells is generally named a "tumor marker." When a substance specifically binding to such a tumor marker is bound to the peptide-based complex of the present invention, the peptide-based complex may be effectively used for tumor diagnosis. Various tumor markers as well as substances capable of specifically binding to the tumor markers are known in the related art.

Also, the tumor markers may be divided into a ligand, antigen, receptor, and nucleic acids encoding the ligand, the antigen, and the receptor, depending on an action mechanism.

When the tumor marker is a "ligand," a substance capable of specifically binding to the ligand may be introduced into the peptide-based complex according to the present invention. In this case, a receptor or an antibody capable of specifically binding to the ligand may be used properly. Examples of the ligand usable in the present invention and the receptor capable of specifically binding to the ligand includes C2 of synaptotagmin and phosphatidyl serine, annexin V and phosphatidyl serine, integrin and a receptor thereof, a vascular endothelial growth factor (VEGF) and a receptor thereof, angiopoietin and a Tie2 receptor, somatostatin and a receptor thereof, and a vasointestinal peptide and a receptor thereof, but the present invention is not particularly limited thereto.

Representative examples of the "receptor" which is the tumor marker include a folic acid receptor expressed in ovarian cancer cells. A substance specifically binding to the receptor (folic acid in case of a folic acid receptor) may be introduced into the peptide-based complex according to the present invention. In this case, a ligand or an antibody capable of specifically binding to the receptor may be used properly.

When the tumor marker is an "antigen," a substance capable of specifically binding to the antigen may be introduced into the peptide-based complex according to the present invention. In this case, an antibody capable of specifically binding to the antigen may be used properly. Examples of the antigen usable in the present invention and the antibody specifically binding to the antigen may include a carcinoembryonic antigen (a colon cancer marker antigen) and Herceptin (Genentech, USA), an HER2/neu antigen (breast cancer marker antigen) and Herceptin, and a prostate-specific membrane antigen (a prostate cancer marker antigen) and Rituxan (IDCE/Genentech, USA).

Such an antibody may be commercially available, or may be prepared according to the methods known in the related art. In general, a mammal (for example, a mouse, a rat, a goat, a rabbit, a horse, or a sheep) is immunized once or more with a proper amount of an antigen. After a predetermined period of time, when a titer reaches a proper level, the antibody is recovered from a serum of the mammal. The recovered antibody may be optionally purified using a known process, and stored in a frozen buffered solution for future use. The details of this method are widely known in the related art.

Meanwhile, the "nucleic acid" includes RNA and DNA, which encode the ligand, the antigen, the receptor, or a fragment thereof as described above. Since the nucleic acid has a characteristic of forming a base pair between complementary sequences as known in the related art, the nucleic acid having a specific base sequence may be detected using a nucleic acid having a base sequence complementary to the base sequence. The nucleic acid having a base sequence complementary to the nucleic acid encoding the enzyme, the ligand, the antigen, or the receptor may be introduced into the peptide-based complex according to the present invention.

Also, the nucleic acid may be effectively used to bind to the cell-penetrating peptide since a functional group such as —$NH_2$, —SH, or —COOH is bound to the 5' and 3' termini of the nucleic acid.

Such a nucleic acid may be synthesized using a standard method known in the related art, for example, an automated DNA synthesizer (for example, a DNA synthesizer commercially available from Biosearch Technologies, Applied BioSystem, and the like). By way of example, a phosphorothioate oligonucleotide may be synthesized using a method disclosed in Stein et al. *Nucl. Acids Res.* 1988, vol. 16, p. 3209. A methylphosphonate oligonucleotide may be prepared using a controlled glass polymer support (Sarin et al. *Proc. Natl. Acad. Sci. U.S.A.* 1988, vol. 85, p. 7448).

Additionally, the present invention is directed to providing a multi-diagnostic probe including the peptide-based complex of the present invention, and a diagnostic probe.

A probe for diagnosing a T1 magnetic resonance image, an optical diagnostic probe, CT diagnostic probe, or radioactive isotope may be used as the diagnostic probe.

For example, the multi-diagnostic probe may be used to perform diagnosis of a T2 magnetic resonance image and a T1 magnetic resonance image at the same time when the probe for diagnosing a T1 magnetic resonance image binds to a fluorescent fusion peptide, perform diagnosis of a magnetic resonance image and an optical image at the same time when the optical diagnostic probe binds to the fluorescent fusion peptide, and perform diagnosis of a magnetic resonance image and a CT diagnostic image at the same time when the CT diagnostic probe binds to the fluorescent fusion peptide. Also, the multi-diagnostic probe may be used to perform diagnosis of a magnetic resonance image, PET and SPECT at the same time when the radioactive isotope binds to the fluorescent fusion peptide.

In this case, the probe for diagnosing a T1 magnetic resonance image includes a Gd compound or an Mn compound, the optical diagnostic probe includes an organic fluorescent dye, quantum dots, or a dye-labeled inorganic support (for example, $SiO_2$, or $Al_2O_3$), the CT diagnostic probe includes an iodine (I) compound or gold nanoparticles, and the radioactive isotope includes In, Tc, or F.

Also, the present invention is directed to providing a cellular therapeutic agent including the peptide-based complex according to the present invention.

When the peptide-based complex according to the present invention is bound to stem cells or immune cells, and transferred into the cells by means of the cell-penetrating peptide, the peptide-based complex may be anchored in cell membranes of target cells, tissues, or organs. As a result, the peptide-based complex according to the present invention has an effect of enhancing a medicinal effect of the cellular therapeutic agent by anchoring the stem cells or immune cells for a long period of time.

The immune cells include macrophages; T cells such as helper T cells, cytotoxic T cells, and suppressor T cells; B cells; and antigen-presenting cells such as dendritic cells, Langerhans cells, and interdigitating follicular cells, but the present invention is not particularly limited thereto.

Also, when the peptide-based complex of the present invention is bound to a fluorescent material directly by means of a chemical, physical covalent or non-covalent bond or indirectly using other mediator, and transferred into cells, the cells may be traced by measuring fluorescence intensity.

Also, when the peptide-based complex of the present invention is bound to a tissue-specific binding component directly by means of a chemical, physical covalent or non-covalent bond or indirectly using other mediator, and transferred into cells, cell targetability may be enhanced.

Also, when the peptide-based complex of the present invention is bound to a pharmaceutically active component, for example, a drug for suppression or treatment of a cardiovascular disease or a brain disease, directly by means of a chemical, physical covalent or non-covalent bond or indirectly using other mediator, and transferred into cells, a therapeutic effect of the cells may be enhanced.

In addition, the present invention is directed to providing a medical stent including the peptide-based complex according to the present invention.

When the peptide-based complex of the present invention is bound to endothelial cells or vascular progenitor cells, and transferred into cells by means of the cell-penetrating peptide, the peptide-based complex may be anchored in the cell membranes of target cells, tissues, or organs. As a result, the peptide-based complex according to the present invention has an effect of enhancing a therapeutic effect of the medical stent by anchoring the endothelial cells or vascular progenitor cells for a long period of time.

Also, when the peptide-based complex of the present invention is bound to a fluorescent material directly by means of a chemical, physical covalent or non-covalent bond or indirectly using other mediator, and transferred into blood vessels, the stent may be traced by measuring fluorescence intensity.

Also, when the peptide-based complex of the present invention is bound to a tissue-specific binding component directly by means of a chemical, physical covalent or non-covalent bond or indirectly using other mediator, and transferred into blood vessels, targetability may be enhanced.

Also, when the peptide-based complex of the present invention is bound to a pharmaceutically active component, for example, a cell growth-inhibiting drug, directly by means of a chemical, physical covalent or non-covalent bond or indirectly using other mediator, and transferred into blood vessels, a therapeutic effect of the stent may be enhanced.

Hereinafter, the present invention will be described in detail by means of Examples. However, it should be understood that the following Example are given by way of illustration of the present invention only, and are not intended to limit the scope of the present invention.

Example 1

Preparation of Peptide-Based Complex Having a Cell-Penetrating Peptide/Cell Membrane Protein/Cell-Penetrating Peptide Structure Using Recombination Method A peptide-based complex was prepared using a pHis/TAT expression vector (Kwon J H et al., 2007, *Biochem Biophys Res Commun.*, 363, 399-404). Using OPRD cDNA as a template and two primers (Primer-1,5'-TCACGTGGATCC-CTGGCAATCGCCATCACCGCG-3' (underlined BamHI site) and Primer-2,5'-AGGCATCTCGAGTTAGCGGC-GGCGCTGGCGGCGTTTCTTGCGGCCGTAAG TGTAC-CGGACGATGCCGAA-3' (underlined XhoI site)), a polymerase chain reaction (PCR) was performed to obtain a DNA fragment. Thereafter, the DNA fragment was separately digested with restriction enzymes (BamHI/XhoI), inserted into a pHis/TAT expression vector, and expressed in *E. coli* strain BL21 (DE3). A protein was then separated and purified using Ni-NTA affinity chromatography. As a result, a bio-pin, in which TAT cell-penetrating peptides were fused with the N-terminus and the C-terminus of a peptide composed of 31 amino acids spanning from a $48^{th}$ amino acid (leucine, L) to a $78^{th}$ amino acid (threonine, T) of the first domain of the OPRD protein composed of 372 amino acids (corresponding to 7 transmembrane domains), was prepared (see FIG. 2: Pin-55).

Also, a bio-pin was prepared in the same manner as in the PCR, except that 5'-TCGTCCCATATGGGATCCCTG-GCAATCGCCATCACC-3' (underlined NdeI site) was used instead of Primer-1 to prepare the bio-pin in which the cell-penetrating peptide was fused with only one end of the OPRD peptide composed of 31 amino acids (BPin-44).

Example 2

Figure 3:
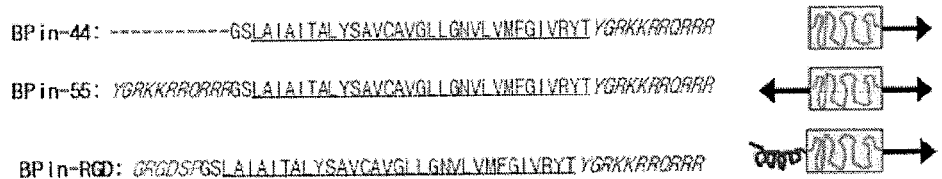
FIG. 3 is a diagram showing structures of the peptide-based complexes according to the present invention, in which the italicized sequences are a TAT-CPP sequence which is a kind of the cell-penetrating peptide and an RGD sequence which is a kind of the cell-adhesive peptide, and the underlined sequences are a fragment of the opioid receptor-δ transmembrane domain 1 (OPRD)

Preparation of Peptide-Based Complex Having a Cell-Penetrating Peptide/Cell Membrane Protein/Cell-Penetrating Peptide Structure Using Peptide Synthesis The peptide-based complex according to the present invention could be prepared using a peptide synthesizer. FIG. 3 shows the sequences of the bio-pins synthesized using the peptide synthesizer by Bio-Synthesis Inc. (USA): a bio-pin (BPin-55) in which the cell-penetrating peptides were fused with both ends of the first domain of the OPRD, and the other BPin-44 in which the cell-penetrating peptide was fused with one end of the first domain of the OPRD.

Experimental Example 1

Transfer of Fluorescent Material-Modified Peptide-Based Complex of Example 1 into Cells Rat cardiac myoblast H9c2 cells ($3 \times 10^4$ cells) were incubated in a DMEM medium supplemented with 10% FCS and an antibiotic agent in a 4-well chamber (Lab-Tek chamber slide, Nunc, USA). The H9c2 cells were stabilized for 24 hours, treated with a cell-labeling dye (Vybrant™ DiI, Invitrogen, USA) at a final concentration of 5 µl/mL, and then kept at 37° C. for 30 minutes in a $CO_2$ incubator. Subsequently, the H9c2 cells were washed three times with phosphate-buffered saline (PBS), and prepared.

Two kinds of the bio-pins (BPin-44 and BPin-55: see FIG. 3) were synthesized by Bio-Synthesis Inc. (USA). Modification of the bio-pin was performed as follows. 0.1 mg of bio-pin peptides (BPin-44 and BPin-55) were treated with 20.6 µl and 15.6 µl of a Dylight 488 NHE-ester dye (Thermo, USA), respectively. The bio-pin peptides were reacted at room temperature for an hour, and then dialyzed (Slide-A-Lyzer Mini Dialysis Units, Thermo, USA) to remove an unreacted fluorescent dye.

The previously prepared H9c2 cells were treated with the bio-pin modified with the Dylight 488 NHE-ester dye at a final concentration of 1 µM, kept at 37° C. for an hour in a $CO_2$ incubator, and then washed three times with PBS. To observe the stained H9c2 cells under a confocal microscope, a cell chamber was treated with a mounting solution (3 drops), and the H9c2 cells were observed under an LSM700 confocal microscope (Carl Zeiss, Germany) at wavelengths of Vybrant™ DiI (red) (Abs 549 nm/Em 565 nm) and Dylight 488 NHE-ester (green) (Abs493 nm/Em 518 nm).

Figure 4:
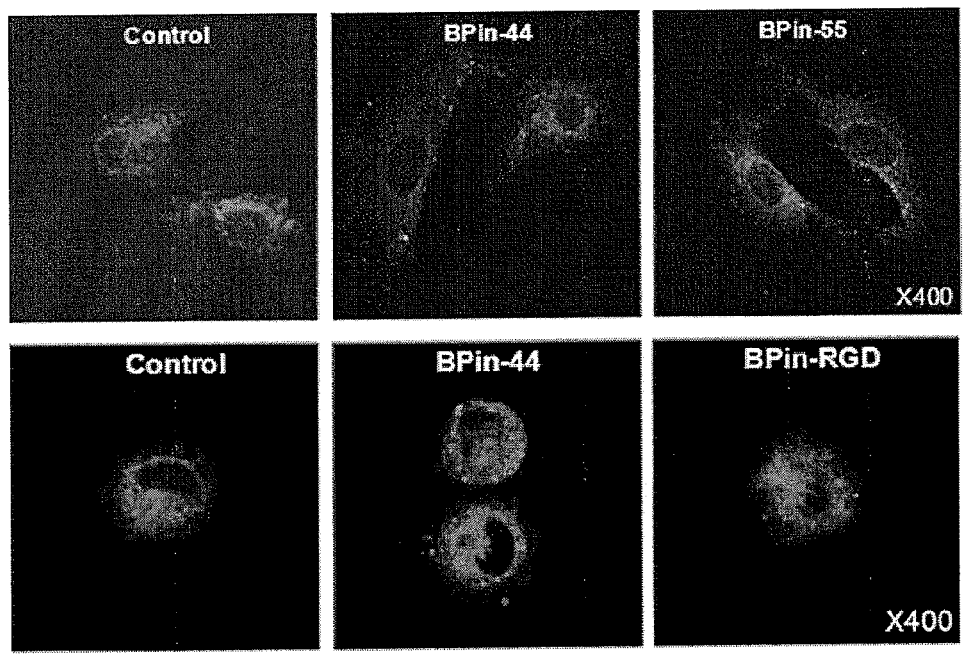
FIG. 4 a confocal microscope image obtained by treating cells with the peptide-based complexes according to the present invention (BPin-44: a bio-pin in which the cell-penetrating peptide is located at the C-terminus of the cell membrane protein; BPin-55: a bio-pin in which the cell-penetrating peptides are located at both ends of the cell membrane protein; and BPin-RGD: a bio-pin in which the cell-penetrating peptide is located at the C-terminus of the cell membrane protein and the cell-adhesive peptide is located at the N-terminus of the cell membrane protein)

As shown in FIG. 4, it was revealed that all of the two bio-pins were positioned in the cell membrane.

Experimental Example 2

Effects of Peptide-Based Complex of Example 1 on Increase in Intercellular Bond Number Rat cardiac myoblast H9c2 cells were incubated until a 4-well chamber (Lab-Tek chamber slide) was 100% filled with the H9c2 cells. Thereafter, the H9c2 cells were treated with a cell-labeled dye (Vybrant™ DiI) at a final concentration of 5 µl/mL, reacted at 37° C. for 30 minutes in a $CO_2$ incubator, and then washed three times with PBS.

Also, rat mesenchymal stem cells were cultured in a MesenPRO (Gibco, USA) medium in a petri dish. Thereafter, trypsin-EDTA and a trypsin-neutralizing solution were added at a ratio of 1:1, and then reacted for 5 minutes to detach the stem cells. The stem cells were treated with a cell-modifying dye (Vybrant™ DiO, Invitrogen, USA) at a final concentration of 5 µl/mL, reacted at 37° C. for 30 minutes in a $CO_2$ incubator, washed three times with PBS, and then centrifuged for 3 minutes at a rotary speed of 1,200 rpm to be prepared.

The prepared stem cells were treated with the peptide-based complex previously prepared in Example 1 or 2 at a final concentration of 1 µM, reacted at 37° C. for an hour in a $CO_2$ incubator while stirring right and left, washed three times with PBS, and then centrifuged to obtain a cell pellet. Subsequently, the cell pellet was re-suspended in 400 µl of a DMEM medium supplemented with 10% FBS. The resulting suspension was spread on the H9c2 cells stained with Vybrant™ DiI, and kept at 37° C. for 10 minutes in a $CO_2$ incubator. Thereafter, the suspension was washed several times with PBS to remove MSCs which were not attached to the H9c2 cells, and the H9c2 cell and MSCs were observed under a fluorescent microscope IX71 (Olympus, USA) at wavelengths of Vybrant™ DiI (red) (Abs 549 nm/Em 565 nm) and Vybrant™ DiO (green) (Abs 488 nm/Em 501 nm), respectively. To quantify the MSCs attached to the H9c2 cells, a cell medium was removed off, and 200 µl of 0.1% Triton X-100 was added, and removed off after 5 minutes. Then, the MSCs attached to the H9c2 cells were observed at absorption/emission wavelengths of 485 nm/535 nm using a fluorescent spectrometer Victor3 (Perkin-Elmer, USA).

Figure 5:
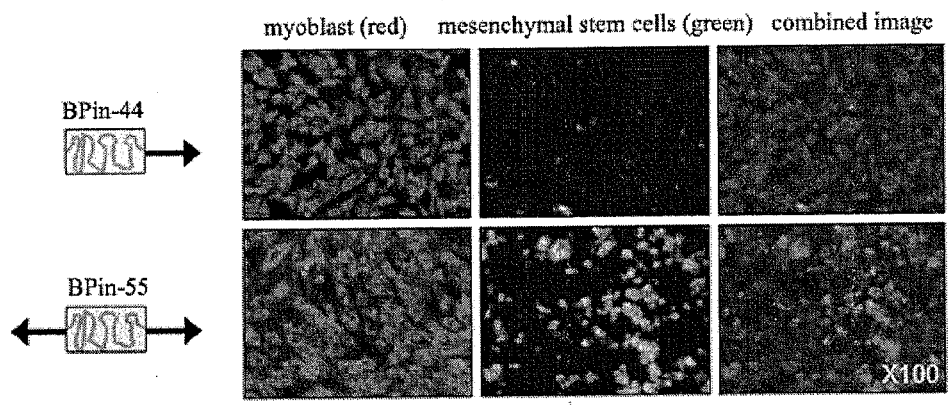
FIGS. 5 and 6 are a fluorescence microscope image (FIG. 5) obtained by treating mesenchymal stem cells of a rat stained with a green fluorescent dye (Dil) with the peptide-based complexes BPin-44 and BPin-55 according to the present invention, respectively, and adhering the mesenchymal stem cells to a petri dish on which cardiac cells H9c2 stained with a red fluorescent dye (DiO) are spread, and a graph (FIG. 6) plotted by measuring absorption/emission values (484 nm/501 nm) using a fluorescent spectrometer.
Figure 6:
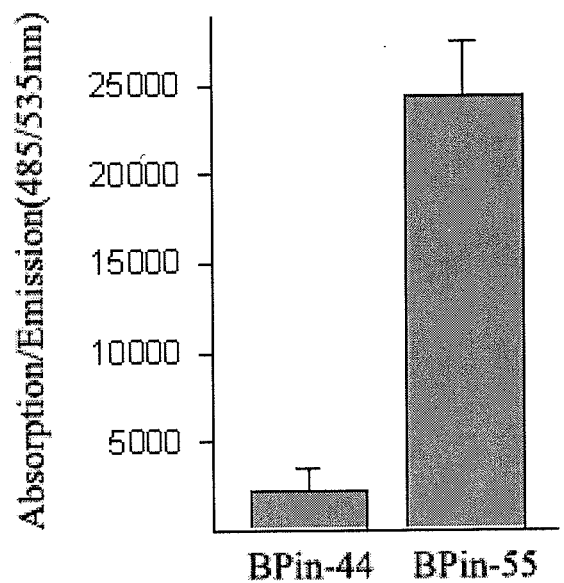

As shown in FIGS. 5 and 6, it was revealed that the number of intercellular bonds was remarkably increased in the experiment group in which the bio-pin BPin-55 was transferred into the H9c2 cells.

Example 3

Preparation of Peptide-Based Complex Having a Cell-Penetrating Peptide/Cell Membrane Protein/Cell-Adhesive Peptide Structure Using Recombination Method A peptide-based complex was prepared using a pHis/TAT expression vector (Kwon J H et al., 2007, *Biochem Biophys Res Commun.*, 363, 399-404). Using OPRD cDNA as a template and two primers (Primer-1,5'-TCGTCC<u>CATATG</u>GGC-CGCGGCGACAGCCCGGG<u>ATCC</u>CTGGCAATCGCCAT-CACC-3' (underlined NdeI site) and Primer-2,5'-AGGCAT-<u>CTCGAG</u>TTAGCGGCGGCGCTGGCGGCGTTTCTTGC-GGCCGTAAGTGTACCGGACGATGCCGAA-3' (underlined XhoI site)), a PCR was performed to obtain a DNA fragment. Thereafter, the DNA fragment was separately digested with restriction enzymes (BamHI/XhoI), inserted into a pHis/TAT expression vector, and expressed in *E. coli* strain BL21 (DE3). A protein was then separated and purified using Ni-NTA affinity chromatography. As result, a bio-pin (BPin-RGD), in which the adhesive peptide (GRGDSP) and the TAT cell-penetrating peptide were fused respectively with the N-terminus and the C-terminus of a peptide composed of 31 amino acids spanning from a $48^{th}$ amino acid (leucine, L) to a $78^{th}$ amino acid (threonine, T) of the first domain of the OPRD protein composed of 372 amino acids (corresponding to 7 transmembrane domains), was prepared (see FIG. 2).

Example 4

Preparation of Peptide-Based Complex Having a Cell-Penetrating Peptide/Cell Membrane Protein/Cell-Adhesive Peptide Structure Using Peptide Synthesis The peptide-based complex according to the present invention could be prepared using a peptide synthesizer. FIG. 3 shows the sequence of the bio-pin synthesized using the peptide synthesizer by Bio-Synthesis Inc. (USA): a bio-pin (BPin-RGD) in which the cell-adhesive peptide and the cell-penetrating peptide were fused with both ends of the first domain of the OPRD.

Experimental Example 3

Transfer of Fluorescent Material-Modified Peptide-Based Complex of Example 3 into Cells Rat cardiac myoblast H9c2 cells cultured in a DMEM medium were put into a microtube, treated with a CellMask™ plasma membrane stain (Invitrogen, USA) at a final concentration of 5 μg/mL, and then kept at 37° C. for 30 minutes in a $CO_2$ incubator. Thereafter, the H9c2 cells were centrifuged, washed three times with phosphate-buffered saline (PBS), and re-suspended with 500 μl of a DMEM medium.

Modification of the peptide (BPin-RGD) was performed as follows. DyLight 405 NHS ester (Thermo, USA) was dissolved in 100 μl of dimethylformamide, and 0.1 mg of the peptide was then added thereto. The bio-pin peptide was reacted at room temperature for an hour, and then dialyzed (Slide-A-Lyzer Mini Dialysis Units, Thermo, USA) to remove an unreacted fluorescent dye.

The previously stained H9c2 cells ($5 \times 10^4$ cells) were treated with the modified peptide at a concentration of 100 nM, and then kept at 37° C. for an hour in a $CO_2$ incubator. Subsequently, the H9c2 cells were centrifuged, and washed three times with PBS. The BPin-44 was used as the control.

To observe the H9c2 cells under a confocal microscope, a cell chamber was treated with a mounting solution (3 drops), and the H9c2 cells were observed under an LSM700 confocal microscope (Carl Zeiss, Germany) at wavelengths of Cell-Mask™ plasma membrane stain (red) (Abs 554 nm/Em 567 nm) and Dylight 405 NHE-ester (blue) (Abs 400 nm/Em420 nm).

As shown in FIG. 4, it was revealed that all the two bio-pins were positioned in the cell membrane.

Experimental Example 4

Effects of Peptide-Based Complex of Example 3 on Increase in Intercellular Bond Number Rat cardiac myoblast H9c2 cells were incubated until a 4-well chamber (Lab-Tek chamber slide) was 100% filled with the H9c2 cells. Thereafter, the H9c2 cells were treated with a CellMask™ plasma membrane stain (Invitrogen, USA) at a final concentration of 5 μl/mL, reacted at 37° C. for 30 minutes in a $CO_2$ incubator, and then washed three times with PBS.

Also, rat mesenchymal stem cells (MSCs) were cultured in in a MesenPRO (Gibco, USA) medium in a petri dish. Thereafter, trypsin-EDTA and a trypsin-neutralizing solution were added at a ratio of 1:1, and then reacted for 5 minutes to detach the stem cells. The stem cells were treated with a cell-modifying dye (Vybrant™ DiO, Invitrogen, USA) at a final concentration of 2 μl/mL, reacted at 37° C. for 30 minutes in a $CO_2$ incubator, washed three times with PBS, and then centrifuged for 3 minutes at a rotary speed of 1,200 rpm.

The prepared stem cells were treated with the bio-pin prepared in Example 3 at a final concentration of 100 nM, reacted at 37° C. for an hour in a $CO_2$ incubator while stirring right and left, washed three times with PBS, and then centrifuged to obtain a cell pellet. Subsequently, the cell pellet was re-suspended in 400 μl of a DMEM medium supplemented with 10% FBS. The resulting suspension was spread on the stained H9c2 cells, and kept at 37° C. for 10 minutes in a $CO_2$ incubator. Thereafter, the suspension was washed several times with PBS to remove MSCs which were not attached to the H9c2 cells. To quantify the MSCs attached to the H9c2 cells, 200 μl of 0.1% Triton X-100 was added, and removed off after 5 minutes. Then, the MSCs attached to the H9c2 cells were observed at absorption and emission wavelengths of 484 nm/501 nm using a fluorescent spectrometer Victor3 (Perkin-Elmer, USA).

Figure 7:
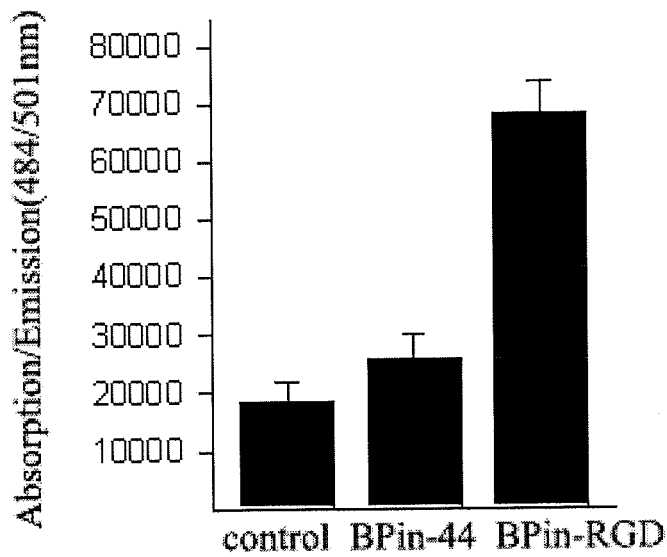
FIG. 7 is a graph plotted by calculating absorption/emission values (484 nm/501 nm) measured using a fluorescent spectrometer after treating mesenchymal stem cells of a rat stained with a green fluorescent dye with the peptide-based complexes BPin-44 and BPin-RGD according to the present invention, respectively, and adhering the mesenchymal stem cells to a petri dish on which cardiac cells are spread.

As shown in FIG. 7, it was revealed that the number of intercellular bonds was remarkably increased in the experiment group in which the bio-pin BPin-RGD was transferred into the H9c2 cells.

Example 5

Preparation of Fluorescent Material-Modified Peptide-Based Complex-Monocyte

DyLight 405 NHS ester (Thermo, USA) was dissolved in 100 μl of dimethylformamide, and 0.1 mg of the peptide BPin-44 was added thereto. The peptide BPin-44 was reacted at room temperature for an hour, and then dialyzed (Slide-A-Lyzer Mini Dialysis Units, Thermo, USA) to remove an unreacted fluorescent dye.

The monocyte THP-1 cells were cultured in an RPMI medium (Gibco, USA) in a petri dish. Thereafter, trypsin-EDTA and a trypsin-neutralizing solution were added at a ratio of 1:1, and then reacted for 5 minutes to detach the THP-1 cells. The THP-1 cells were treated with a cell-modifying dye (Vybrant™ DiO, Invitrogen, USA) at a final concentration of 2 μl/mL, reacted at 37° C. for 30 minutes in a $CO_2$ incubator, washed three times with PBS, and then centrifuged for 3 minutes at a rotary speed of 1,200 rpm.

The THP-1 cells ($5 \times 10^4$ cells) were treated with the peptide (BPin-44) modified with a fluorescent material at a concentration of 100 nM, and then kept at 37° C. for an hour in a $CO_2$ incubator. Subsequently, the THP-1 cells were centrifuged, and washed three times with PBS.

Experimental Example 5

Examination of Binding Affinity of Fluorescent Material-Modified Peptide-Based Complex-Monocyte of Example 5 to Endothelial Cells HUVECs ($5 \times 10^4$ cells/well) were cultured in an EGM medium (Lonza, USA) on a 24-well plate, starved for 4 hours in a 0.5% EBM medium, and treated with TNF-alpha (10 ng/mL) for 24 hours. Thereafter, the HUVECs were treated with a CellMask™ plasma membrane stain (Invitrogen, USA) at a final concentration of 5 μg/mL, reacted at 37° C. for 30 minutes in a $CO_2$ incubator, and then washed three times with PBS.

The prepared HUVECs were treated with the THP-1 cells treated with the fluorescent material-modified peptide prepared in Example 5, and re-suspended in 400 μl of a DMEM medium supplemented with 10% FBS. The resulting suspension was spread on the stained HUVECs, and then kept at 37° C. for 30 minutes in a $CO_2$ incubator. Thereafter, the suspension was washed several times with PBS to remove unattached THP-1 cells. To quantify the THP-1 cells attached to the HUVECs, 200 μl of 0.1% Triton X-100 was added, and removed off after 5 minutes. Then, the THP-1 cells attached to the HUVECs were observed at absorption/emission wavelengths of 484 nm/501 nm using a fluorescent spectrometer Victor3 (Perkin-Elmer, USA).

Figure 8:
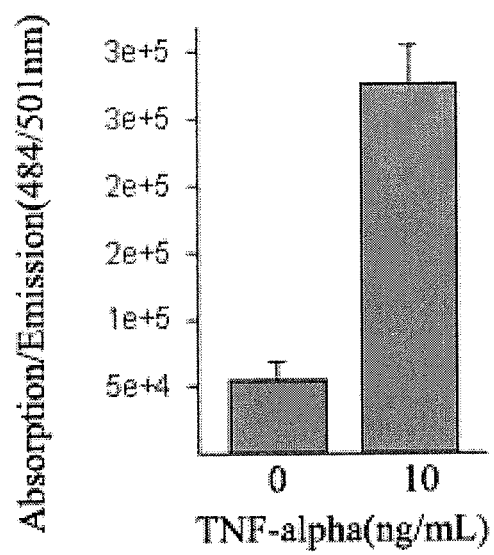
FIG. 8 is a graph plotted from absorption/emission values (484 nm/501 nm) measured using a fluorescent spectrometer after adhering monocyte THP-1 cells, which are bound to the peptide-based complex BPin-44 of the present invention modified with Dylight 405 NHE-ester, and stained with a green fluorescent dye, to endothelial cells treated with TNF-alpha.

As shown in FIG. 8, it was revealed that the binding affinity was increased compared with that of the control (endothelial cells not exposed to stimuli) when the monocytes bound to the fluorescent material-modified peptide were treated to the endothelial cells stimulated with TNF-alpha.

Figure 9:
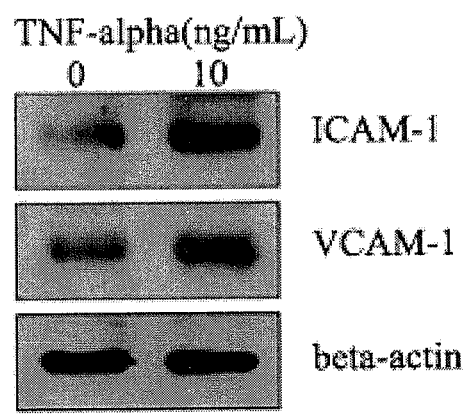
FIG. 9 is a diagram showing levels of ICAM-1 and VCAM-1 increased by TNF-alpha through the immunoblotting results of a cell lysate of HUVECs shown in FIG. 8.

Also, to determine whether the HUVECs were suitably stimulated with TNF-alpha, immunoblotting was performed using anti-ICAM-1 and anti-VCAM-1 antibodies. As a result, it was confirmed that intercellular cell adhesion molecule-1 (ICAM-1) and vascular cell adhesion molecule-1 (VCAM-1) were increasingly expressed by the TNF-alpha (FIG. 9).

In addition, to determine whether the fluorescent dye-modified BPin-44 was actually anchored in the THP-1 cells bound onto the HUVECs, 3D images were obtained from simultaneously photographed images of the HUVECs and the THP-1 and simultaneously photographed images of the HUVECs and the fluorescent dye-modified BPin-44. As a result, it was confirmed that the THP-1 cells were observed in the same position as the fluorescent dye-modified BPin-44 (FIG. 10).

The peptide-based complex according to the present invention is a bio-pin which may be effectively transferred into the cells, serves to increase intercellular bonds, and thus can be effectively used as a material for diagnosis or treatment of diseases since the peptide-based complex is applicable to drug or cell transfer, cell treatment, molecular imaging, a medical appliance, and the like.

Also, the peptide-based complex according to the present invention can be useful in simultaneously diagnosing or treating diseases by specifically recognizing a lesion site of a specific disease, for example, arteriosclerosis or tumor and binding to cells of the lesion site.

Accordingly, the present invention can be used as a cellular therapeutic agent or a diagnostic contrast agent, and used in a medical appliance.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A peptide-based complex represented by the following Structural Formula 1 or 2, wherein the peptide-based complex is modified with a fluorescent material:

[Structural Formula 1]

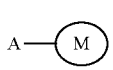

[Structural Formula 2]

wherein, A and B each independently represent a cell-penetrating peptide, cell-adhesive peptide, or a cell-penetrating or cell-adhesive peptide bound to a monocyte or an oncotropic cell, and A' represents a cell-penetrating or cell-adhesive peptide bound to a monocyte or an oncotropic cell, and M represents a cell membrane protein, wherein, A and B bind to both ends of the cell membrane protein.

2. The peptide-based complex of claim 1, wherein the cell membrane protein comprises opioid receptor-delta (δ) transmembrane domain 1 (OPRD TM1).

3. The peptide-based complex of claim 1, wherein the cell membrane protein has an amino acid sequence set forth in SEQ ID NO: 1.

4. The peptide-based complex of claim 1, wherein the cell-penetrating peptide is at least one selected from the group consisting of a trans-activating transcriptional activator (Tat), Antp, Mph-1, VP22, and HP4.

5. The peptide-based complex of claim 1, wherein the cell-adhesive peptide is at least one selected from the group consisting of amino acid sequences set forth in SEQ ID NO: 3 (RGDS), SEQ ID NO: 4 (KQAGDV), SEQ ID NO: 5 (VAPG), SEQ ID NO: 6 (YAVTGRGDSPAS, FIB1), SEQ ID NO: 7 (ATLQLQEGRLHFXFDLGKGR, EFlzz), SEQ ID NO: 8 (AGTFALRGDNPQG, A99), and SEQ ID NO: 9 (GEFYFDLRLKGDKY, 531).

6. The peptide-based complex of claim 1, wherein the oncotropic cell is a natural killer cell or a macrophage.

7. The peptide-based complex of claim 1, wherein the fluorescent material is at least one selected from the group consisting of a Dylight 488 NHE-ester dye, Vybrant™ DiI, Vybrant™ DiO, quantum-dot nanoparticles, Cy3.5, Cy5, Cy5.5, Cy7, indocyanine green (ICG), Cypate, ITCC, NIR820, NIR2, IRDye78, IRDye80, IRDye82, Cresy Violet, Nile Blue, Oxazine 750, rhodamine 800, lanthanide, and Texas Red.

8. The peptide-based complex of claim 1, wherein a pharmaceutically active component is further bound to the peptide-based complex.

9. The peptide-based complex of claim 8, wherein the pharmaceutically active component is at least one selected from the group consisting of siRNA, antisense, an anti-cancer agent, an antibiotic agent, a hormone, a hormone antagonist, an interleukin, an interferon, a growth factor, a tumor necrosis factor, an endotoxin, a lymphotoxin, urokinase, streptokinase, a tissue plasminogen activator, a protease inhibitor, alkylphosphocholine, a component labeled with a radioactive isotope, a cardiovascular drug, a gastrointestinal drug, and a nervous system drug.

10. The peptide-based complex of claim 1, wherein a tissue-specific binding component is further bound to the peptide-based complex.

11. The peptide-based complex of claim 10, wherein the tissue-specific binding component is at least one selected from the group consisting of an antigen, an antibody, RNA, DNA, a hapten, avidin, streptavidin, neutravidin, Protein A, Protein G, a lectin, a selectin, a radioactive isotope-labeled component, and a material which can specifically bind to a tumor marker.

12. A contrast agent composition comprising the peptide-based complex of claim 1.

13. A targeted contrast agent composition comprising the peptide-based complex of claim 1.

14. A composition for simultaneous diagnosis or treatment, which comprises the peptide-based complex of claim 1.

15. A multi-diagnostic probe comprising the peptide-based complex of claim 1.

16. A cellular therapeutic agent comprising the peptide-based complex of claim 1.

17. A medical stent comprising the peptide-based complex of claim 1.

* * * * *